United States Patent
Kawaguchi et al.

(10) Patent No.: US 6,921,368 B2
(45) Date of Patent: Jul. 26, 2005

(54) BLOOD PRESSURE MONITOR APPARATUS

(75) Inventors: Keizoh Kawaguchi, Komaki (JP); Atsushi Sato, Komaki (JP)

(73) Assignee: Colin Medical Technology Corporation, Komaki (JP)

( * ) Notice: Subject to any disclaimer, the term of this patent is extended or adjusted under 35 U.S.C. 154(b) by 122 days.

(21) Appl. No.: 10/370,696

(22) Filed: Feb. 24, 2003

(65) Prior Publication Data

US 2004/0019284 A1 Jan. 29, 2004

(30) Foreign Application Priority Data

Jul. 26, 2002 (JP) ........................................ 2002-218282

(51) Int. Cl.[7] .................................................. A61B 5/02
(52) U.S. Cl. ..................................................... 600/485
(58) Field of Search ................................. 600/481, 483, 600/485, 490, 492–496

(56) References Cited

U.S. PATENT DOCUMENTS

| | | | |
|---|---|---|---|
| 5,566,676 A | * 10/1996 | Rosenfeldt et al. | ......... 600/485 |
| 5,752,913 A | 5/1998 | Oka | |
| 6,027,455 A | 2/2000 | Inukai et al. | |
| 6,120,456 A | 9/2000 | Oka et al. | |
| 6,190,325 B1 | * 2/2001 | Narimatsu | ................... 600/490 |
| 6,491,638 B2 | * 12/2002 | Oka | ........................... 600/494 |
| 6,500,127 B1 | * 12/2002 | Inukai et al. | ............... 600/485 |
| 6,740,044 B2 | * 5/2004 | Sato | ........................... 600/485 |

FOREIGN PATENT DOCUMENTS

| | | |
|---|---|---|
| EP | 0 990 418 A1 | 4/2000 |
| EP | 0 997 102 A1 | 5/2000 |
| EP | 0 997 103 A1 | 5/2000 |
| EP | 1 161 920 A2 | 12/2001 |
| JP | A-11-318837 | 11/1999 |

* cited by examiner

*Primary Examiner*—Robert L. Nasser
*Assistant Examiner*—Navin Natnithithadha
(74) *Attorney, Agent, or Firm*—Oliff & Berridge, PLC (57) ABSTRACT

A blood pressure monitor apparatus for monitoring a blood pressure of a living subject, wherein the blood pressure is judged to be abnormal when a first change value as a change of each of a plurality of blood pressure values iteratively obtained from the subject, from a standard blood pressure obtained from the subject, does not fall in a first reference range (TH1), wherein the improvement comprises: the first reference range being determined based on the standard blood pressure of the subject, according to a relationship between first reference range and standard blood pressure wherein a plurality of different first reference ranges correspond to a plurality of different standard blood pressures, respectively.

7 Claims, 7 Drawing Sheets

BLOOD PRESSURE MONITOR APPARATUS

BACKGROUND OF THE INVENTION

1. Field of the Invention

The present invention relates to a blood pressure monitor apparatus which monitors blood pressure values iteratively obtained from a living subject.

2. Related Art Statement

A blood pressure monitor apparatus is used, for instance, for continuously monitoring the blood pressure of a patient or a living subject during an operation. One example of the blood pressure monitor apparatus is adapted to judge the abnormality of blood pressure of the subject when the blood pressure is higher than a predetermined upper threshold or lower than a predetermined lower threshold. Another example of the blood pressure monitor apparatus is adapted to determine, as a standard blood pressure of the subject, a blood pressure measured at a certain time point, and judge the abnormality of the blood pressure of the subject when an amount or a rate of change of the blood pressure of the subject from the standard blood pressure does not fall in a prescribed reference range. For instance, JP-A-11-318837 or its corresponding U.S. Pat. No. 6,027,455 discloses a technique to judge the abnormality of blood pressure of the subject, wherein 1) an estimated blood pressure is iteratively determined based on pulse-wave-propagation-velocity-related information which is related to a velocity at which a pulse wave propagates in the subject, and the abnormality of blood pressure of the subject is judged when the iteratively determined estimated blood pressure does not fall in a prescribed alert range, and 2) a blood pressure obtained at a prescribed period by using a cuff is determined as a standard blood pressure, and the abnormality of blood pressure of the subject is judged when a rate of change of the iteratively determined estimated blood pressure from the standard blood pressure does not fall in a prescribed reference range.

Where the abnormality of blood pressure of the subject is judged when the blood pressure is higher than the prescribed upper threshold or lower than the prescribed lower threshold, the abnormality of blood pressure is not found so long as the changed (increased or decreased) blood pressure falls within a normal or permissible range defined by the upper and lower thresholds, even if the change (increase or decrease) of the blood pressure may be large. In this case, an abrupt or rapid change of the physical condition of the patient may not be quickly detected. Where the abnormality of blood pressure is judged when the amount or rate of change of the blood pressure of the patient from the standard blood pressure does not fall in the prescribed reference range, the blood pressure of the subject may be judged to be abnormal even if the blood pressure may fall in the normal or permissible range. In this arrangement, however, the blood pressure of the patient may be judged to be abnormal even if the change of the blood pressure from the standard blood pressure may be toward a normal value. For instance, where the standard blood pressure is as low as the lower threshold of the normal range, it is not necessary to judge the abnormality of blood pressure even in the event of a great increase of the blood pressure. On the other hand, where the standard blood pressure is as high as the upper threshold of the normal range, it is not necessary to judge the abnormality of blood pressure even in the event of a great decrease of the blood pressure. However, the conventional blood pressure monitor apparatus described above judges that the blood pressure is abnormal when the amount or rate of change of the blood pressure from the standard blood pressure does not fall in the prescribed reference range, irrespective of the magnitude of the standard blood pressure. Thus, the conventional blood pressure monitor apparatus may judge the abnormality of blood pressure even in the above-described cases where a great increase or decrease of the blood pressure is not abnormal.

SUMMARY OF THE INVENTION

It is therefore an object of the present invention to provide a blood pressure monitor apparatus capable of judging an abnormality of a blood pressure of a living subject with high accuracy.

The above-indicated object of the present invention has been achieved by the present invention. According to the present invention, there is provided a blood pressure monitor apparatus for monitoring a blood pressure of a living subject, wherein the blood pressure is judged to be abnormal when a first change value, which is determined as a change of each of a plurality of blood pressure values iteratively obtained from a standard blood pressure obtained from the subject, does not fall in a first reference range, wherein the improvement comprises: the first reference range being determined based on the standard blood pressure of the subject, according to a relationship between first reference range and standard blood pressure wherein a plurality of different first reference ranges correspond to a plurality of different standard blood pressures, respectively.

In the present blood pressure monitor apparatus, the first reference range is determined based on the standard blood pressure obtained from the living subject, according to the relationship wherein a plurality of different first reference ranges correspond to a plurality of different standard blood pressures. Accordingly, the first reference range changes with the standard blood pressure, so that the abnormality of blood pressure can be judged with high accuracy.

In the case where an anesthesiologist judges the abnormality of blood pressure of a patient during an operation, his or her criteria for judgment of abnormal blood pressure may differ from those of other anesthesiologists. Further, the judgment of abnormal blood pressure made by the anesthesiologist may vary depending upon various factors such as the kind of the operation, or the physical power and age of the patient. In view of this, the above-indicated relationship between first reference range and standard blood pressure is preferably determined by an operator of the blood pressure monitor apparatus. According to this arrangement, the relationship between first reference range and standard blood pressure is determined by the operator of the apparatus depending upon the circumstances. Accordingly, the relationship can be determined for each specific operation, for instance, in view of a medical judgment of a doctor in charge, the kind of the operation, and the physical power and age of each specific patient who undergoes the operation. Therefore, the present arrangement assures that the first reference range is appropriately determined according to the thus determined relationship, and that the abnormality of blood pressure of the patient is accurately judged.

According to another preferred feature of the invention, the relationship between first reference range and standard blood pressure is recorded on a recording medium which is attachable to, and detachable from, the apparatus. According to this arrangement, the recording medium on which the above-described relationship is recorded can be installed on another blood pressure monitor apparatus, whereby the same blood pressure monitoring operation can be carried out in that apparatus. Further, if the relationship is recorded on a plurality of recording media, the plurality of recording media can be installed on respective blood pressure monitor apparatuses, whereby the same blood pressure monitoring operation can be carried out in the plurality of monitor apparatuses.

The above-described relationship between first reference range and standard blood pressure may be determined in advance. The first reference range is defined by at least one of an upper first threshold which is used to judge whether an increase of the blood pressure is abnormal, and a lower first threshold which is used to judge whether a decrease of the blood pressure is abnormal.

Where the first reference range is defined by the upper first threshold and the relationship between upper first threshold and standard blood pressure is determined, the relationship is preferably determined such that a smaller upper first threshold corresponds to a higher standard blood pressure. According to this arrangement wherein the upper first threshold decreases with the increase in the standard blood pressure obtained from the subject, the apparatus judges that the blood pressure of the subject is abnormal even if an increase of the blood pressure may be small where the standard blood pressure is high. On the other hand, the apparatus does not judge that the blood pressure is abnormal even if an increase of the blood pressure may be large where the standard blood pressure is low. Therefore, the present arrangement assures an accurate judgment of abnormal blood pressure.

Where the first reference range is defined by the lower first threshold and the relationship between lower first threshold and the standard blood pressure is determined, the relationship is preferably determined such that a greater lower first threshold corresponds to a lower standard blood pressure obtained from the subject, in other words, a smaller absolute value of lower first threshold corresponds to a lower standard blood pressure. According to this arrangement wherein the lower first threshold increases with the decrease of the standard blood pressure, in other words, the absolute value of the lower first threshold decreases with the decrease of the standard blood pressure, the apparatus judges that the blood pressure of the subject is abnormal even if a decrease of the blood pressure may be small where the standard blood pressure is low, while the apparatus does not judge that the blood pressure is abnormal even if a decrease of the blood pressure may be large where the standard blood pressure is high. Therefore, the present arrangement assures an accurate judgment of abnormal blood pressure.

In still another preferred feature of the invention, the blood pressure of the subject is judged to be abnormal when a second change value as a change of the above-indicated each of the blood pressure values from a blood pressure value obtained a predetermined time period before the each of the blood pressure values does not fall in a second reference range. According to this arrangement, the blood pressure of the subject is judged to be abnormal based on not only the change of the each of the iteratively obtained blood pressure values from the standard blood pressure, but also the change of the each of the iteratively obtained blood pressure values from the blood pressure value obtained the predetermined time period before the each of the iteratively obtained blood pressure values. Thus, the blood pressure monitor apparatus according to the present feature is capable of accurately judging the abnormality of blood pressure of the subject.

In yet another preferred feature of the invention, the blood pressure of the subject is judged to be abnormal when the each of the blood pressure values does not fall in a third reference range. According to this arrangement, the blood pressure of the subject can be judged to be abnormal based on the each of the iteratively obtained blood pressure values itself, irrespective of the change of blood pressure of the subject. Accordingly, the blood pressure monitor apparatus according to the present feature is capable of accurately judging the abnormality of blood pressure of the subject.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which.

DETAILED DESCRIPTION OF PREFERRED EMBODIMENTS

Figure 1:
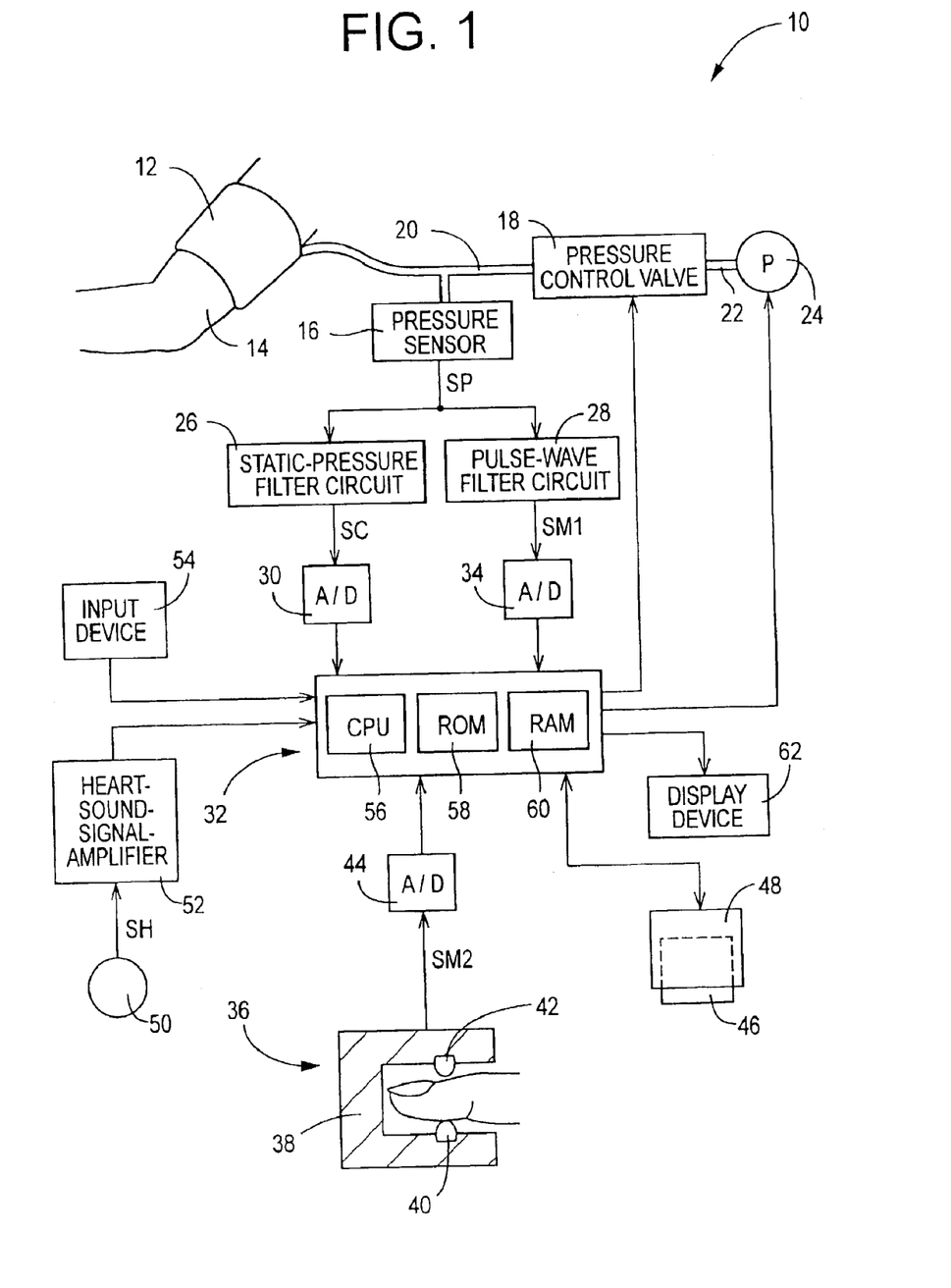
FIG. 1 is a diagrammatic view for explaining a construction of a blood pressure monitor apparatus to which the present invention is applied.

Hereinafter, there will be described one embodiment of the present invention, by reference to the drawings. FIG. 1 is a diagrammatic view for explaining the construction of a blood pressure (BP) monitor apparatus 10 to which the present invention is applied. The BP monitor apparatus 10 is used, for instance, to monitor a blood pressure of a patient who is undergoing an operation.

As shown in FIG. 1, the present BP monitor apparatus 10 includes a cuff 12 which has a belt-like cloth bag and a rubber bag accommodated in the cloth bag and which is adapted to be wound around an upper arm 14 of a patient as a living subject, a pressure sensor 16 and a pressure control valve 18. The pressure sensor 16 and the pressure control valve 18 are connected to the cuff 12 via a piping 20. An air pump 24 is connected to the pressure control valve 18 via a piping 22. The pressure control valve 18 adjusts a pressure of a pressurized air supplied from the air pump 24, and supplies the pressure-adjusted air to the cuff 12, or discharges the pressurized air from the cuff 12, so as to control an air pressure in the cuff 12.

The pressure sensor 16 detects the air pressure in the cuff 12, and supplies a pressure signal SP representing the detected air pressure, to a static-pressure filter circuit 26 and a pulse-wave filter circuit 28. The static-pressure filter circuit 26 has a low-pass filter and extracts, from the pressure signal SP, a cuff-pressure signal SC representing a static-pressure component contained in the signal SP, i.e., a pressing pressure of the cuff 12 (hereinafter referred to as "cuff pressure PC"). The cuff-pressure signal SC is supplied to an electronic control device 32 which will be described, via an analog-to-digital (AID) converter 30. The pulse-wave filter circuit 28 includes a band-pass filter which transmits a frequency component of the pressure signal SP that has frequencies in a range of about 1 to 30 Hz, and extracts, from the pressure signal SP, a cuff-pulse-wave signal SM1. The cuff-pulse-wave signal SM1 is supplied to the control device 32 via an A/D converter 34. The cuff-pulse-wave signal SM1 represents an upper-arm pulse wave which is transmitted from the upper arm 14 to the cuff 12.

The BP monitor apparatus 10 further includes: a photoelectric-pulse-wave detecting sensor 36; a reading and recording device 48 to and from which a recording medium 46 is attached and detached; a heart-sound microphone 50; a heart-sound-signal amplifier 52; an input device 54; the electronic control device 32; and a display device 62.

The photoelectric-pulse-wave detecting sensor 36 functions as a volumetric pulse-wave detecting device which detects a volumetric pulse wave (plethysmograph) from peripheral blood vessels of the subject, and may have a construction similar to that of one which is used to detect pulse. The photoelectric-pulse-wave detecting sensor 36 is worn on a body portion of the subject, i.e., an end portion of a finger of an arm of the subject around which the cuff 12 is not wound. The sensor 36 includes: a housing 38 which can accommodate a body portion of the subject; a light-emitting element 40 as a light source which emits, toward a skin of the subject, a red or infrared light in such a wavelength band that can be reflected by hemoglobin, preferably a light having a wavelength of about 800 nm that is not influenced by blood oxygen saturation; and a light-receiving element 42 which is opposed to the light-emitting element 40 and detects the light transmitted through the body portion. The sensor 36 outputs a photoelectric pulse-wave signal SM2 representing respective instantaneous volumes of the blood present in the capillaries of the body portion, and supplies the signal SM2 to the control device 32 via an A/D converter 44.

On the recording medium 46 such as a memory card, a photomagnetic disc, a compact disc, a flexible disc, etc., there is recorded a relationship between first reference range TH1 and standard blood pressure $BP_{ST}$ that is used to determine a first reference range TH1 for judging an abnormality of a first change value indicative of a change of each of a plurality of blood pressure values iteratively obtained from the subject, from a standard blood pressure $BP_{ST}$ obtained from the subject. This relationship will be described in greater detail, later. The recording medium 46 is attachable to, and detachable from, the reading and recording device 48 which has functions of: reading information from the recording medium 46 and outputting the information read from the recording medium 46 to the control device 32; and recording, on the recording medium 46, the relationship obtained on the basis of data inputted through the input device 54.

The heart-sound microphone 50 is fixed, with an adhesive tape, not shown, to a prescribed location on a chest of a living subject. The microphone 50 accommodates a piezo-electric element, not shown, which converts heart sounds produced from the heart of the subject, into an electric signal, i.e., a heart-sound signal SH. The heart-sound-signal amplifier 52 includes four sorts of filters, not shown, which cooperate with one another to attenuate a low-pitch component having a great energy and thereby amplifies and filters a high-pitch component of the heart-sound signal SH. The heart-sound signal SH outputted from the amplifier 52 is supplied to the electronic control device 32 via an A/D converter, not shown.

The input device 54 includes a plurality of keys through which a plurality of sorts of information are inputted. The plurality of sorts of information include a stature T of the subject; the above-described relationship between first reference range and standard blood pressure; a time period used for calculating a second change value (which will be described in greater detail) indicative of a change of each of the iteratively obtained blood pressure values during the time period; a second reference range TH2 used for judging whether or not the second change value is abnormal; and a third reference range TH3 used for judging whether or not each of the blood pressure values iteratively obtained from the subject is abnormal. The input device 54 outputs, to the control device 32, signals respectively representing the plurality of sorts of information inputted through the keys.

The electronic control device 32 is essentially provided by a so-called microcomputer including a CPU (central processing unit) 56, a ROM (read only memory) 58, a RAM (random access memory) 60, an input-and-output (I/O) port, not shown, etc, and the CPU 56 processes signals according to control programs pre-stored in the ROM 58, while utilizing a temporary-storage function of the RAM 60. The control device 32 outputs, from the I/O port, drive signals to the air pump 24 and the pressure control valve 18 so as to control the respective operations thereof and thereby control the cuff pressure PC. In addition, the CPU 56 iteratively determines a blood pressure BP and an estimated blood pressure EBP according to the control functions shown in FIG. 2, and controls the display device 62 to iteratively display the determined blood pressure BP and estimated blood pressure EBP. Further, the CPU 56 carries out a blood pressure monitoring operation based on the determined blood pressure BP and estimated blood pressure EBP.

Figure 2:
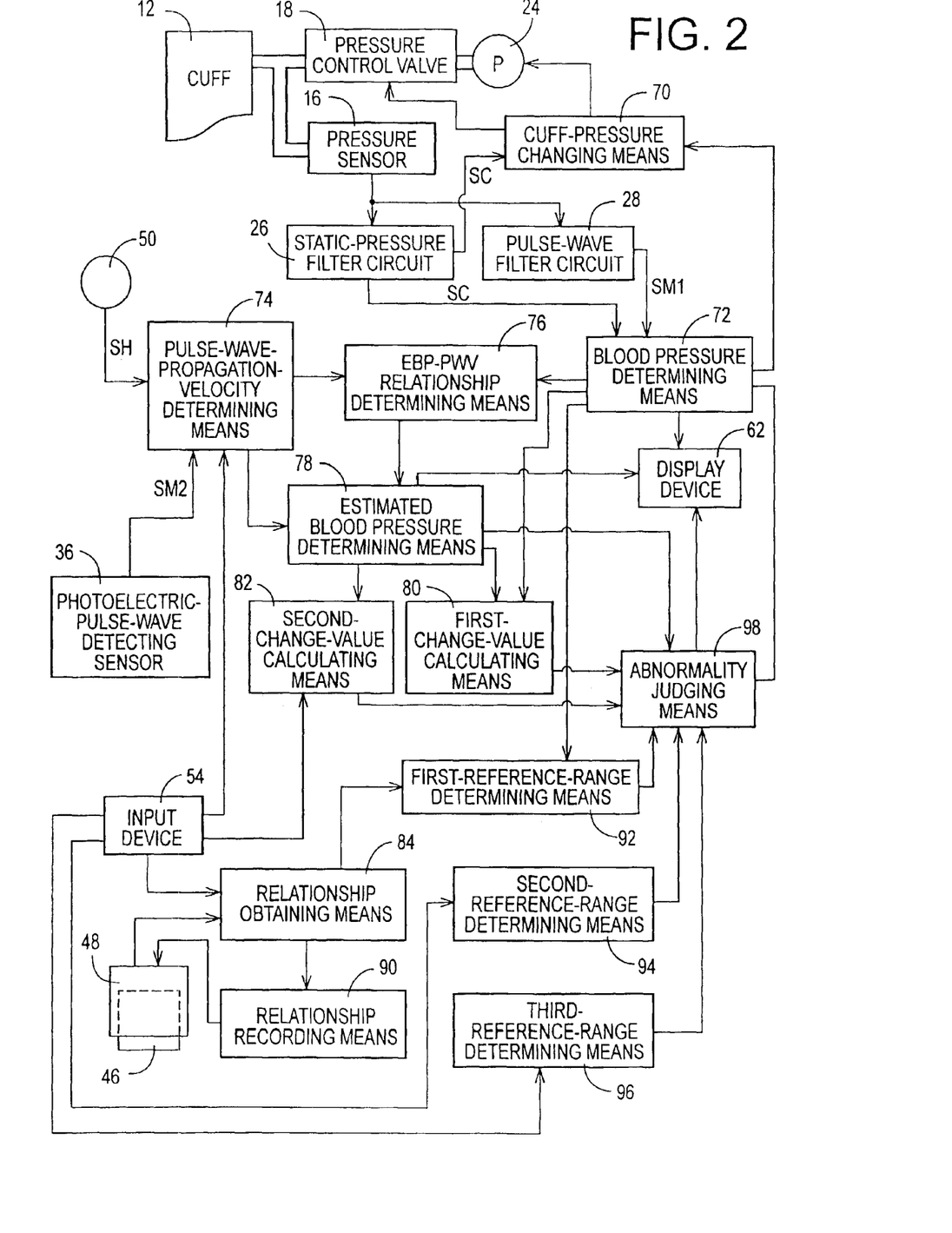
FIG. 2 is a block diagram for explaining essential control functions of a CPU (central processing unit) of a control device of the apparatus of FIG. 1.

FIG. 2 is a block diagram for explaining essential control functions of the CPU 56 of the present BP monitor apparatus 10.

A cuff-pressure changing means or device 70 operates, based on the cuff-pressure signal SC supplied from the static-pressure filter circuit 26, the pressure control valve 18 and the air pump 24 so as to quickly increase the cuff pressure PC to a prescribed target pressure $PC_M$ (e.g., 180 mmHg) that would be higher than a systolic blood pressure $BP_{SYS}$ of the subject and, subsequently, slowly decrease the cuff pressure at a rate of, e.g., 2 or 3 mmHg/sec. After a blood-pressure determining means or device 72, described below, determines a blood pressure BP of the subject, the cuff-pressure changing means 70 releases the cuff pressure PC to an atmospheric pressure.

After a prescribed calibration period $T_C$ set at about 20 to 30 minutes has passed or when the blood pressure of the subject is judged to be abnormal by an abnormality judging means or device 98 described below, the blood pressure determining means 72 determines, according to a well-known oscillometric algorithm, a systolic blood pressure value $BP_{SYS}$, a mean blood pressure value $BP_{MEAN}$, and a diastolic blood pressure value $BP_{DIA}$ of the upper arm 14, based on the cuff pressure PC represented by the cuff-pressure signal SC and the upper-arm pulse wave represented by the cuff pulse-wave signal SM1, which signals SC and SM1 are continuously supplied from the static-pressure filter circuit 26 and the pulse-wave filter circuit, 28, respectively, during the slow decreasing of the cuff pressure PC under the control of the cuff-pressure changing means 70. The thus determined blood pressure values $BP_{SYS}$, $BP_{MEAN}$, $BP_{DIA}$ are displayed by the display device 62.

A pulse-wave-propagation-velocity determining means or device 74 which functions as a pulse-wave-propagation-velocity-related information obtaining means obtains a time difference between a time of detection of a prescribed periodic portion (e.g., a start point of a heart sound I) of each heart-sound waveform iteratively detected by the heart-sound microphone 50, and a time of detection of a prescribed periodic portion of a corresponding photoelectric pulse wave iteratively detected by the photoelectric-pulse-wave detecting sensor 36. This time difference is a pulse-wave-propagation time DT (second) which is needed for the pulse wave to propagate from the heart to a position where the sensor 36 is worn on the subject.

Further, the pulse-wave-propagation-velocity determining means 74 substitutes the subject's stature T supplied from the input device 54, with the following Expression (1) which represents a relationship between propagation distance L and stature T and which is pre-stored in the ROM 58, thereby obtaining a propagation distance L from the heart of the subject to the position where the sensor 36 is worn. The pulse-wave-propagation-velocity determining means 74 additionally substitutes the propagation distance L and the propagation time DT obtained as described above, with the following Expression (2), thereby obtaining a pulse-wave propagation velocity PWV (cm/sec):

$$L=aT+b \quad \text{Expression (1)}$$

(a and b are experimentally determined constants)

$$PWV=L/DT \quad \text{Expression (2)}$$

An EBP (estimated blood pressure)-PWV (pulse-wave propagation velocity) relationship determining means or device 76 determines two coefficients α and β in the following Expression (3) for calculating an estimated blood pressure value EBP, based on any one of the systolic blood pressure value $BP_{SYS}$, mean blood pressure value $BP_{MEAN}$, and diastolic blood pressure value $BP_{DIA}$ determined by the blood pressure determining means 72, and the pulse-wave propagation velocity PWV determined by the pulse-wave-propagation-velocity determining means 74 during, immediately before, or immediately after, the blood pressure measurement period. Expression (3) represents a relationship between estimated blood pressure EBP and pulse-wave propagation velocity PWV. The EBP-PWV relationship is determined based on one set of data consisting of the systolic blood pressure $BP_{SYS}$ and the pulse-wave propagation velocity PWV obtained immediately after the blood pressure measurement period, and another set of data consisting of the systolic blood pressure $BP_{SYS}$ and the pulse-wave propagation velocity PUV determined in the prior blood pressure measurement period.

$$EBP=\alpha \times PWV+\beta \quad \text{Expression (3)}$$

Where the systolic blood pressure $BP_{SYS}$ is used to determine Expression (3) representing the above-indicated EBP-PWV relationship between estimated blood pressure and pulse-wave propagation velocity, the estimated blood pressure EBP obtained from Expression (3) is an estimated systolic blood pressure $EBP_{SYS}$. Where the mean blood pressure $BP_{MEAN}$ is used to determine Expression (3), the estimated blood pressure EBP obtained from Expression (3) is an estimated mean blood pressure $EBP_{MEAN}$. Where the diastolic blood pressure $BP_{DIA}$ is used to determine Expression (3), the estimated blood pressure EBP obtained from Expression (3) is an estimated diastolic blood pressure $EBP_{DIA}$. In short, the EBP-PWV relationship between estimated blood pressure and pulse-wave propagation velocity is determined depending upon which one of the systolic, mean, and diastolic blood pressure values is selected as an estimated (monitor) blood pressure EBP.

An estimated blood pressure determining means or device 78 substitutes the pulse-wave propagation velocity PWV iteratively determined by the pulse-wave-propagation-velocity determining means 74, with Expression (3) determined by the EBP-PWV relationship determining means 76, and thereby iteratively determines an estimated blood pressure value EBP as a non-invasively obtained blood pressure value of the subject. The thus determined estimated blood pressure EBP is iteratively displayed by the display device 62. While the estimated blood pressure EBP is preferably determined at a relatively short period corresponding to one pulse or several pulses, the estimated blood pressure EBP may be determined at any suitable period which is shorter than the above-described calibration period $T_C$.

A first-change-value calculating means or device 80 determines, as a standard blood pressure $BP_{ST}$, one of the systolic blood pressure $BP_{SYS}$, mean blood pressure $BP_{MEAN}$, and diastolic blood pressure $BP_{DIA}$ determined by the BP determining means 72, which one is employed by the EBP-PWV relationship determining means 76 for determining the EBP-PWV relationship between estimated blood pressure and pulse-wave propagation velocity, and iteratively calculates a first change value as a change of each of the estimated blood pressure values EBP iteratively determined by the EBP determining means 78 from the standard blood pressure $BP_{ST}$. The first change value is a rate of change, or an amount of change, of each of the estimated blood pressure values EBP from the standard blood pressure $BP_{ST}$.

A second-change-value calculating means or device 82 calculates a second change value as a change of the each of the estimated blood pressures values EBP determined by the EBP determining means 78 from an estimated blood pressure value EBP determined a predetermined time period before the each of the estimated blood pressure values EBP. The above-described predetermined time period used for determining the second change value (hereinafter referred to as "second-change-value-related time period") may be inputted through the input device 54, or may be a prescribed constant value. It is preferable that the second-change-value-related time period be sufficiently shorter than the above-described calibration period $T_C$. For instance, the second-change-value-related time period is preferably not longer than ten minutes, more preferably not longer than five minutes. The second-change-value-related time period which is a short time period described above is effective to accurately detect an abrupt change of the blood pressure of the subject.

Figure 3:
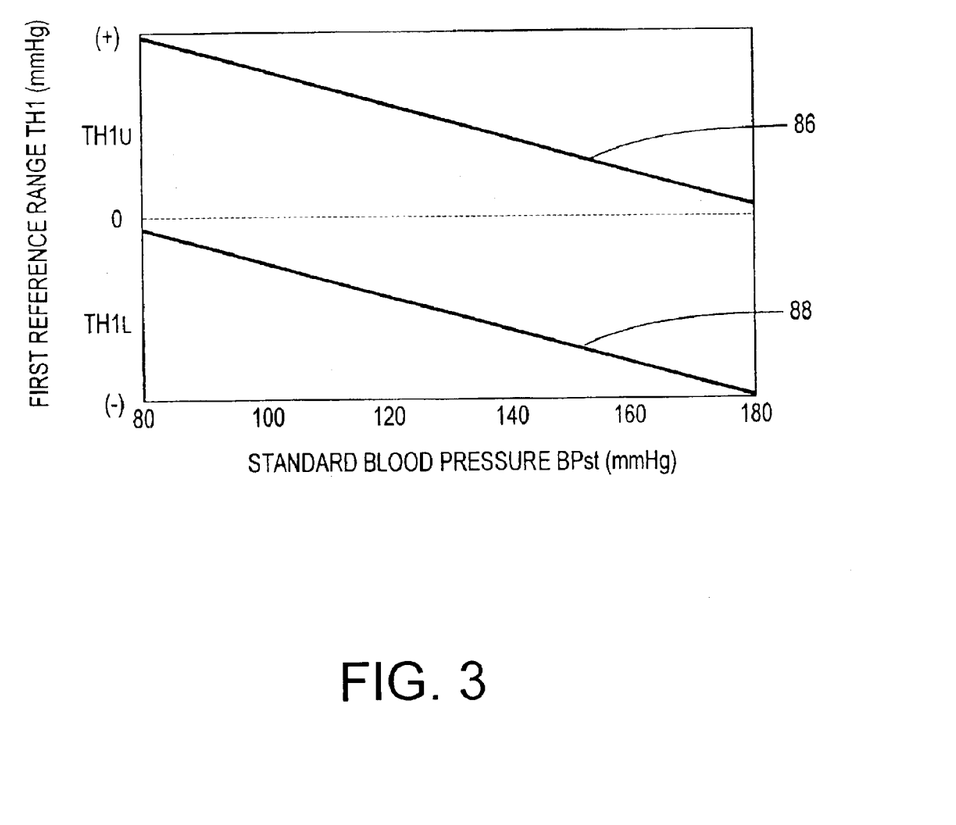
FIG. 3 is a view for explaining a relationship between first reference range and standard blood pressure, which relationship is recorded on a recording medium shown in FIG. 1.

A relationship obtaining means or device 84 obtains, as a relationship between first reference range and standard blood pressure to be used in a current blood pressure monitoring operation, a relationship between first reference range and standard blood pressure which has been read from the recording medium 46 by the reading and recording device 48 or which has been inputted through the input device 54. The graph of FIG. 3 shows one example of the relationship between first reference range TH1 and standard blood pressure $BP_{ST}$ recorded on the recording medium 46. The relationship shown in the graph of FIG. 3 includes an upper-first-threshold relationship 86 for determining an upper first threshold $TH1_U$, and a lower-first-threshold relationship 88 for determining a lower first threshold $TH1_L$. The two relationships 86, 88 are represented by respective straight lines in the graph of FIG. 3. The upper first threshold $TH1_U$ is used to judge whether an increase of the blood pressure of the subject is abnormal. The upper-first-threshold relationship 86 is determined such that the upper first threshold $TH1_U$ linearly decreases with the increase of the standard blood pressure $BP_{ST}$. The lower first threshold $TH1_L$ is used to judge whether a decrease of the blood pressure of the subject is abnormal. The lower-first-threshold relationship 88 is determined such that the lower first threshold $TH1_L$ linearly increases, in other words, the absolute value of the lower first threshold $TH1_L$ linearly decreases, with the decrease of the standard blood pressure $BP_{ST}$. In the relationship shown in the graph of FIG. 3, the straight line representing the upper-first-threshold relationship 86 and the straight line representing the lower-first-threshold relationship 88 are parallel to each other.

The upper-first-threshold relationship 86 and the lower-first-threshold relationship 88 are determined such that the upper first threshold $TH1_U$ and the lower first threshold $TH1_L$ continuously change with the change of the standard blood pressure $BP_{ST}$. However, those relationships 86, 88 may be determined such that the upper first threshold $TH1_U$ and the lower first threshold $TH1_L$ change in steps with the change of the standard blood pressure $BP_{ST}$. In this case, the upper-first-threshold relationship 86 is defined by at least two upper first thresholds $TH1_U$ and the lower-first-threshold relationship 88 is defined by at least two lower first thresholds $TH1_L$, so as to correspond to at least two different standard blood pressures $BP_{ST}$.

A relationship recording means or device 90 records, on the recording medium 46 installed on the reading and recording device 48, the relationship between first reference range and standard blood pressure when the relationship is inputted through the input device 54.

A first-reference-range determining means or device 92 determines, according to the relationship between the first reference range and standard blood pressure obtained by the relationship obtaining means 84, a first reference range TH1 which corresponds to the standard blood pressure $BP_{ST}$, namely, one of the three blood pressure values $BP_{SYS}$, $BP_{MEAN}$, $BP_{DIA}$, each determined by the BP determining means 72, which one is used by the EBP-PWV relationship determining means 76 to determine the EBP-PWV relationship between estimated blood pressure and pulse-wave propagation velocity. The thus determined first reference range TH1 is used to monitor the blood pressure of the subject.

A second-reference-range determining means or device 94 and a third-reference-range determining means or device 96 determine a second reference range TH2 and a third reference range TH3, respectively, based on the input signals supplied from the input device 54.

An abnormality judging means or device 98 judges that the blood pressure of the subject is abnormal, when the estimated blood pressure EBP iteratively determined by the EBP determining means 78 does not fall in the third reference range TH3 determined by the third-reference-range determining means 96, when the first change value iteratively calculated by the first-change-value calculating means 80 does not fall in the first reference range TH1 determined by the first-reference-range determining means 92, or when the second change value iteratively calculated by the second-change-value calculating means 82 does not fall in the second reference range TH2 determined by the second-reference-range determining means 94. When the blood pressure of the subject is judged to be abnormal by the abnormality Judging means 98, the control device 32 operates the display device 64 to display characters or symbols indicating the abnormality of the blood pressure, and operates the blood-pressure determining means 72 to start a reliable blood pressure measurement using the cuff 12.

Figure 4:
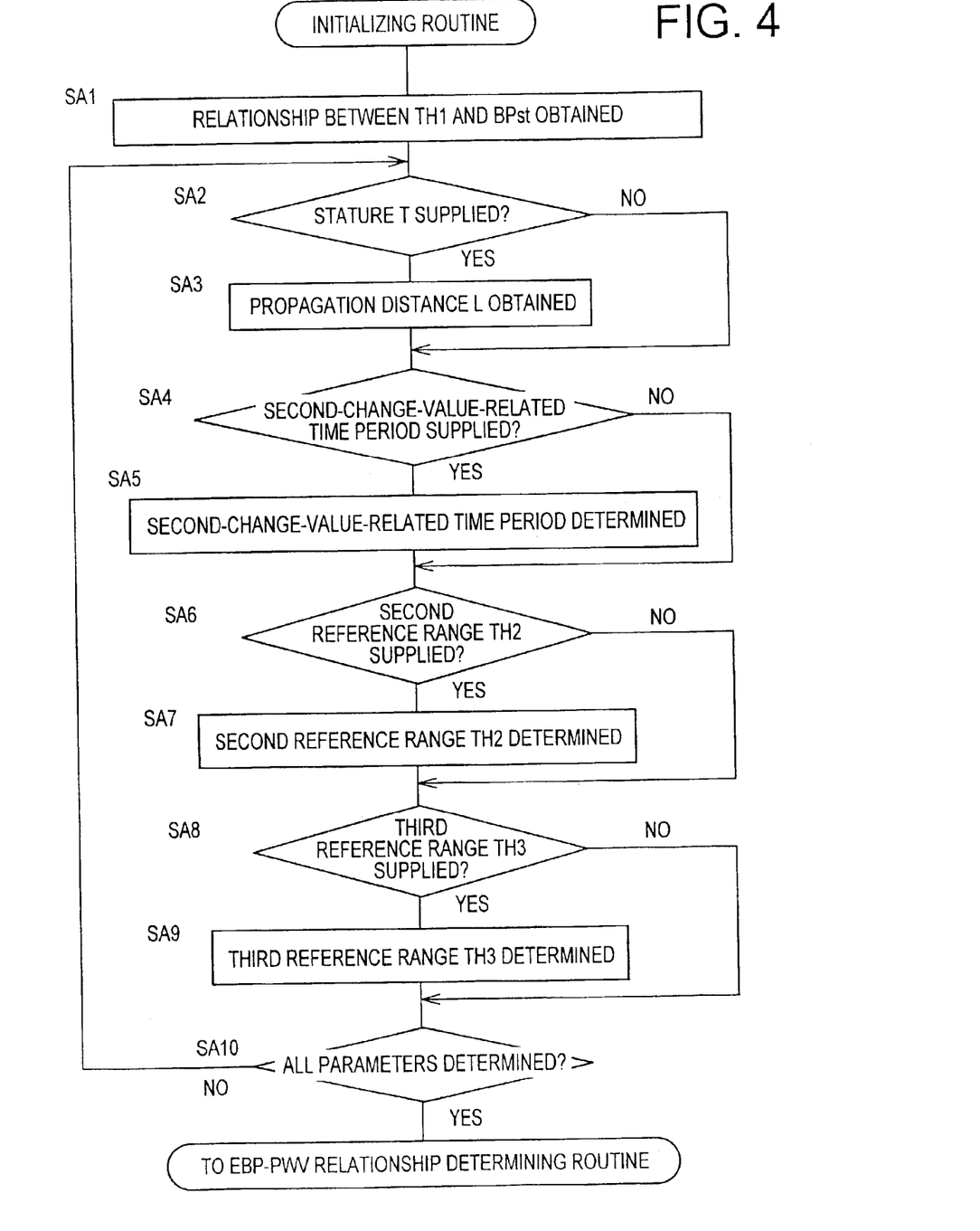
FIG. 4 is a flow chart for explaining more concretely a portion of the control functions of the CPU, shown in the diagrammatic view of FIG. 2, the flow chart representing an initializing routine for obtaining the relationship between first reference range and standard blood pressure, and other control parameters.
Figure 5:
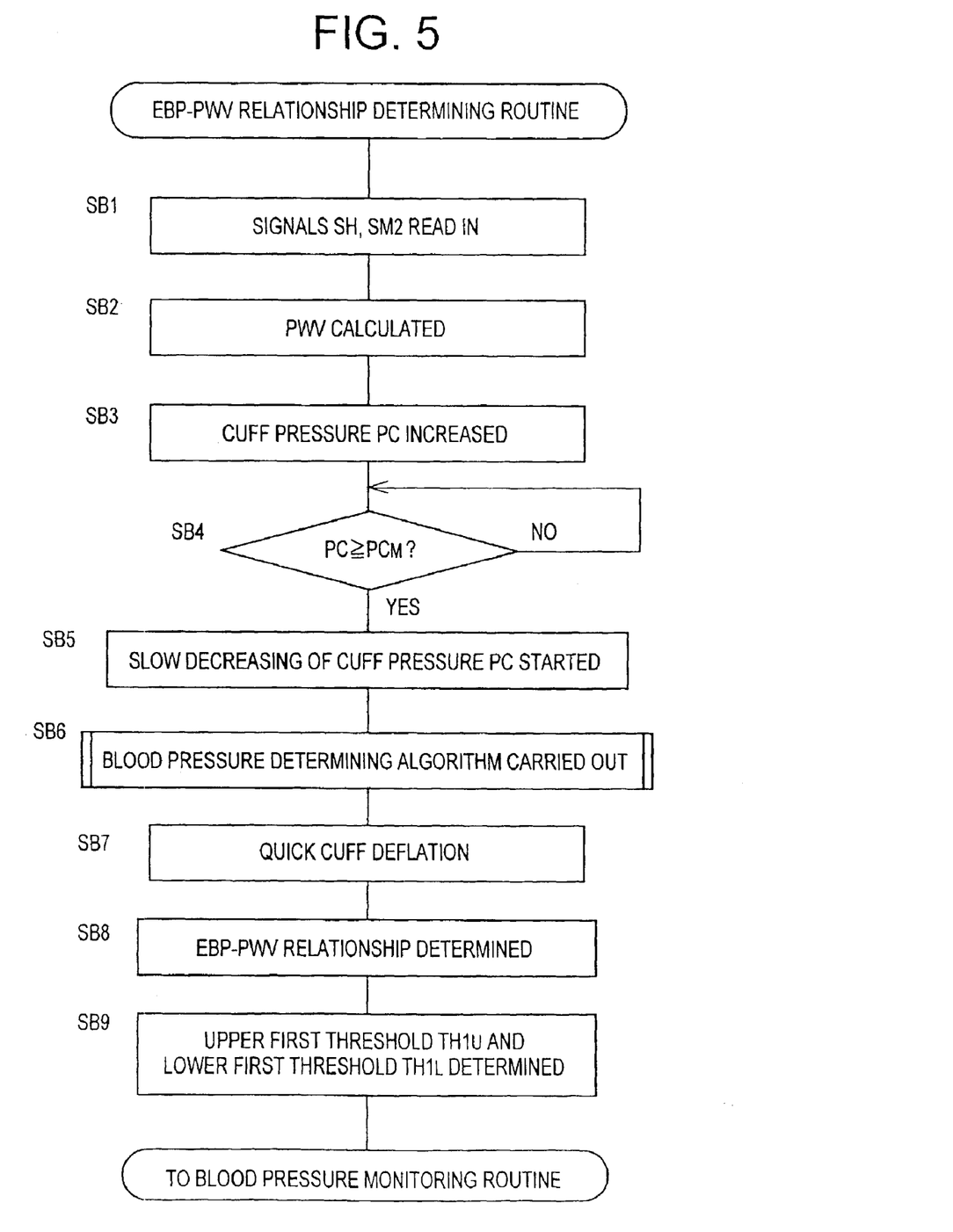
FIG. 5 is a flow chart for explaining more concretely another portion of the control functions of the CPU, shown in the diagrammatic view of FIG. 2, the flow chart representing an EBP-PWV relationship determining routine for determining an EBP-PWV relationship between estimated blood pressure and pulse-wave propagation velocity.
Figure 6:
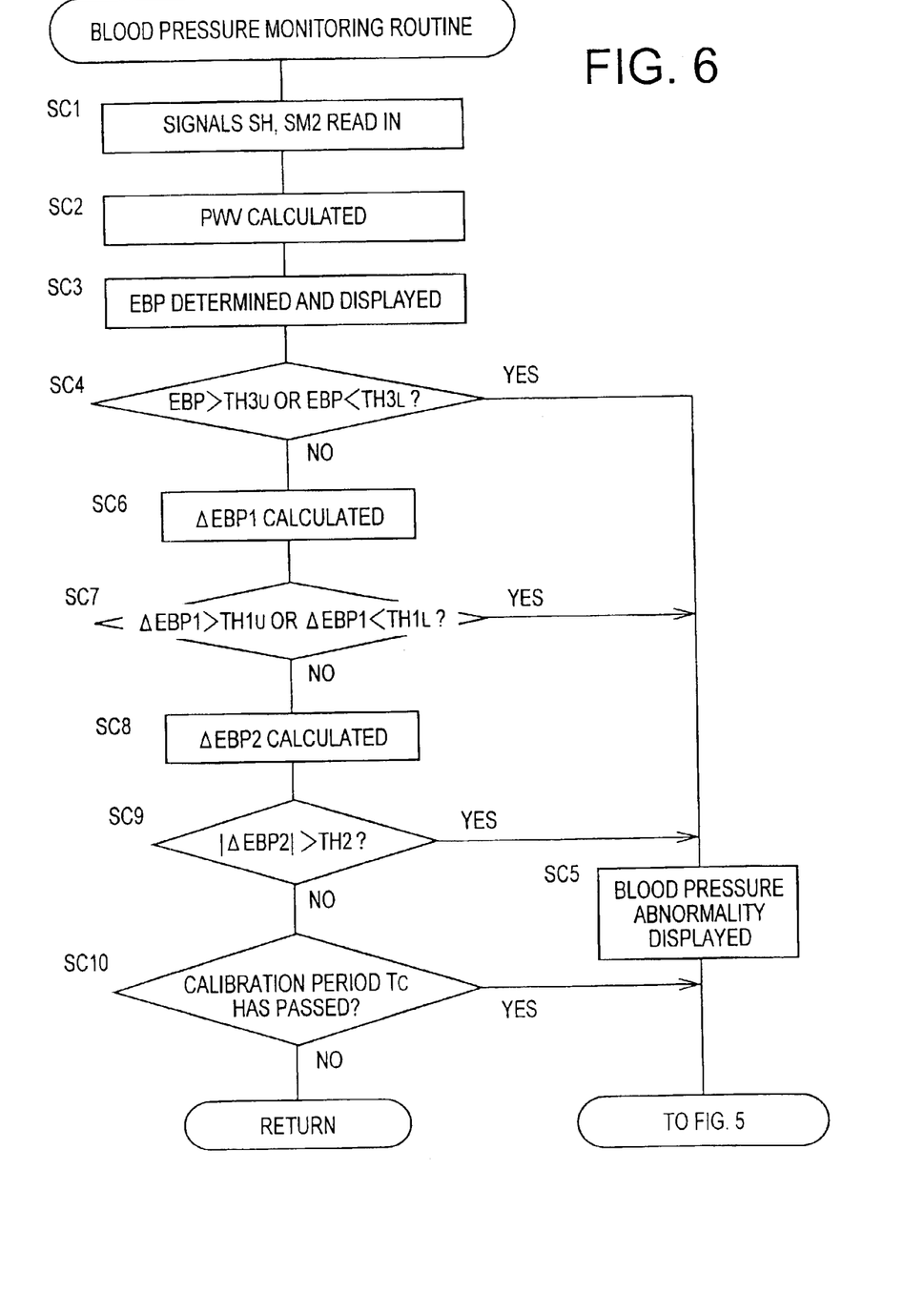
FIG. 6 is a flow chart for explaining more concretely still another portion of the control functions of the CPU, shown in the diagrammatic view of FIG. 2, the flow chart representing a blood pressure monitoring routine.

FIGS. 4 through 6 are flow charts for explaining the control functions of the CPU 56, illustrated in the block diagram of FIG. 2. The flow chart of FIG. 4 shows an initializing routine for obtaining the relationship between first reference range and standard blood pressure, described above. The flow chart of FIG. 5 shows an EBP-PWV relationship determining routine for determining the EBP-PWV relationship described above and determining the upper first threshold $TH1_U$ and the lower first threshold $TH1_L$. The flow chart of FIG. 6 shows a blood pressure monitoring routine for monitoring the blood pressure of the subject based on the estimated blood pressure EBP determined for each pulse.

There will be first explained the initializing routine of FIG. 4. The CPU 56 carries out Step SA1 (hereinafter, "Step" is omitted, if appropriate) corresponding to the relationship obtaining means 84. At SA1, the CPU 56 reads in the relationship between first reference range and standard blood pressure from the recording medium 46 installed on the reading and recording device 48, and determines the relationship which has been read from the recording medium 46 as a relationship between first reference range and standard blood pressure to be used in the current blood pressure monitoring operation. Where the relationship is inputted through the input device 54, the CPU 56 determines the inputted relationship as the relationship to be used in the current blood pressure monitoring operation. Here, it is assumed that the CPU 56 obtains the relationship shown in the graph of FIG. 3.

SA1 is followed by SA2 to judge whether or not a signal indicative of the stature T of the subject has been supplied from the input device 54. If a negative judgment is made at SA2, the control of the CPU 56 goes to SA4 and the following steps. If a positive or affirmative judgment is made at SA2, SA3 is implemented to substitute the stature T with Expression (1), and calculate a propagation distance L from the heart of the subject to the position where the photoelectric-pulse-wave detecting sensor 36 is worn.

Subsequently, the CPU carries out SA4 to judge whether or not the second-change-value-related time period has been inputted through the input device 54. If a negative judgment is made at SA4, the control of the CPU 56 goes to SAG and the following steps. If an affirmative judgment is made at SA4, the control of the CPU 56 goes to SA5 to determine the value inputted through the input device 54 as the second-change-value-related time period. Herein it is assumed that the second-change-value-related time period is set at four minutes.

Subsequently, the CPU 56 carries out SA6 to judge whether or not a second reference range TH2 has been inputted through the input device 54. If a negative judgment is made at SA6, the control of the CPU 56 goes to SA8 and the following steps. If an affirmative judgment is made at SA6, the CPU 56 carries out SA7 corresponding to the second-reference-range determining means 94. At SA7, the CPU 56 determines the second reference range TH2 which has been inputted through the input device 54 as a second reference range TH2 to be used in the current blood pressure monitoring operation. Here, it is assumed that the second reference range TH2 is defined by a second reference value TH2 equal to 40 mmHg.

SA7 is followed by SA8 to judge whether or not a third reference range TH3 has been inputted through the input device 54. If a negative judgment is made at SA8, the CPU 56 carries out SA10. If an affirmative judgment is made at SA8, the control of the CPU 56 goes to SA9 corresponding to the third-reference-range determining means 96. At SA9, the CPU 56 determines the third reference range TH3 which has been inputted through the input device 54, as a third reference range TH3 to be used in the current blood pressure monitoring operation. Here, it is assumed that the third reference range TH3 is defined by an upper third threshold $TH3_U$ set at 180 mmHg, and a lower third threshold $TH3_L$ set at 80 mmHg.

SA9 is followed by SA10 to judge whether or not all of the propagation distance L, second-change-value-related time period, second reference range TH2, and third reference range TH3 have been determined. If a negative judgment is made at SA9, the CPU 56 repeats SA2 and the following steps. If an affirmative judgment is made at SA10, the CPU 56 carries out the EBP-PWV relationship determining routine shown in FIG. 5.

The control of the CPU 56 begins with SB1 of the EBP-PWV relationship determining routine of FIG. 5, where the CPU 56 reads in respective one-heartbeat lengths of the heart-sound signal SH supplied from the heart-sound microphone 50 and the photoelectric-pulse-wave signal SM2 supplied from the sensor 36.

Subsequently, the CPU 56 carries out SB2 corresponding to the pulse-wave-propagation-velocity determining means 74. At SB2, the CPU 56 determines a start point of a heart sound I in the heart-sound waveform represented by the heart-sound signal SH read in at SB1 and a rising point of the photoelectric pulse-wave represented by the photoelectric-pulse-wave signal SM2 read in at SB1, and obtains, as a pulse-wave-propagation time DT, a time difference between a time of detection of the start point of the heart-sound I and a time of detection of the rising point of the photoelectric pulse wave. Then, the CPU 56 substitutes the thus obtained pulse-wave-propagation time DT and the propagation distance L calculated at SA3 of the control routine of FIG. 4, with Expression (2), thereby determining a pulse-wave propagation velocity PWV.

SB2 is followed by SB3 where the CPU 56 drives the air pump 24 and operates the pressure control valve 18, so as to start quickly increasing the cuff pressure PC. Subsequently, at SB4, the CPU 56 judges whether the cuff pressure PC is equal to or higher than a prescribed target pressure value $PC_M$ (i.e., 180 mmHg). If a negative judgment is made at SB4, the CPU 56 repeats this step and continues increasing the cuff pressure PC. In the meantime, if an affirmative judgment is made at SB4, the control flow goes to SB5 to stop the air pump 24 and operate the pressure control valve 18 so as to slowly decrease the cuff pressure PC at a rate of about 3 mmHg/sec.

SB5 is followed by SB6 corresponding to the BP pressure determining means 72. At SB6, a systolic blood pressure value $BP_{SYS}$, a mean blood pressure value $BP_{MEAN}$, and a diastolic blood pressure value $BP_{DIA}$ are determined according to a well known oscillometric BP determining algorithm, based on the variation of respective amplitudes of successive heartbeat-synchronous pulses of the upper-arm pulse wave (cuff pulse wave) represented by the cuff-pulse-wave signal SM1 continuously obtained while the cuff pressure PC is slowly decreased. The determined blood pressure values $BP_{SYS}$, $BP_{MEAN}$, and $BP_{DIA}$ are displayed by the display device 62.

After the blood pressure values have been determined at SB6, SB7 is implemented to switch the pressure control valve 18 to its quick-deflation position, so that the cuff pressure PC is quickly lowered to an atmospheric pressure. In the control routine of FIG. 5, SB3 through SB5, and SB7 correspond to the cuff-pressure changing means 70.

Subsequently, the CPU 56 carries out SB8 corresponding to the EBP-PWV relationship determining means 76. At SB8, the constants α and β in Expression (3) are determined based on one set of data consisting of the pulse-wave propagation velocity PWV obtained at SB2 and the systolic blood pressure $BP_{SYS}$ obtained at SB6, and another set of data obtained at SB2 and SB6 in the prior control cycle according to the EBP-PWV relationship determining routine of FIG. 5. Where the EBP-PWV relationship determining routine is executed for the first time, a standard pulse-wave propagation velocity PWV and a standard systolic blood pressure $BP_{SYS}$ which are pre-stored in the ROM 58 are used as the above-indicated another set of data.

Subsequently, the CPU 56 carries out SB9 corresponding to the first-reference-range determining means 92. At SB9, the CPU 56 determines, as a standard blood pressure $BP_{ST}$, the systolic blood pressure $BP_{SYS}$ determined at SB6. The CPU 56 further determines, according to the relationship (shown in the graph of FIG. 3) obtained at SA1 of the control routine of FIG. 4, the upper first threshold $TH1_U$ and the lower first threshold $TH1_L$ corresponding to the systolic blood pressure $BP_{SYS}$, i.e., the standard blood pressure $BP_{ST}$, as an upper first threshold $TH1_U$ and a lower first threshold $TH1_L$ to be used in the blood pressure monitoring routine of FIG. 6. The upper first threshold $TH1_U$ and the lower first threshold $TH1_L$ which are determined according to the relationship shown in the graph of FIG. 3 change such that, with the increase of the systolic blood pressure $BP_{SYS}$ obtained at SB6, the upper first threshold $TH1_U$ decreases and the lower first threshold $TH1_L$ decreases, namely, the absolute value of the lower first threshold $TH1_L$ increases. In other words, the upper first threshold $TH1_U$ and the lower first threshold $TH1_L$ change such that, with the decrease of the systolic blood pressure $BP_{SYS}$, the upper first threshold $TH1_U$ increases and the lower first threshold $TH1_L$ increases, namely, the absolute value of the lower first threshold $TH1_L$ decreases.

Subsequently, the CPU 56 carries out the blood pressure monitoring routine shown in FIG. 6. The CPU 56 carries out SC1 and SC2 which are the same as SB1 and SB2 of the control routine of FIG. 5, thereby determining a pulse-wave propagation velocity PVW. Described more specifically, at SC1, the CPU 56 reads in respective one-heartbeat lengths of the heart-sound signal SH and the photoelectric-pulse-wave signal SM2. At SC2 corresponding to the pulse-wave-propagation-velocity determining means 74, the CPU 56 determines the pulse-wave propagation velocity PWV based on the signals read in at SC1.

SC2 is followed by SC3 corresponding to the estimated blood pressure (EBP) determining means 78. At SC3, the CPU 56 substitutes the pulse-wave propagation velocity PWV obtained at SC2, with Expression (3) indicative of the EBP-PWV relationship determined at SB8 of the control routine of FIG. 5, and determines an estimated blood pressure EBP. The thus determined estimated blood pressure EBP is displayed by the display device 62.

Subsequently, the control of the CPU 56 goes to SC4 to judge whether the estimated blood pressure EBP determined at SC3 falls within the third reference range TH3 determined at SA9 in the control routine of FIG. 4. Described in detail, the CPU 56 judges at SC4 whether the estimated blood pressure EBP determined at SC3 is greater than the upper third threshold $TH3_U$ determined at SA9 (i.e., 180 mmHg in this embodiment) or smaller than the lower third threshold $TH3_L$ determined at SA9 (i.e., 80 mmHg in this embodiment). If an affirmative judgment is made at SC4, there is a high possibility that the blood pressure of the subject is abnormal. In this case, the CPU 56 carries out SC5 to operate the display device 62 to indicate the abnormality of blood pressure, and carries out again the EBP-PWV relationship determining routine of FIG. 5 so as to quickly obtain a reliable blood pressure BP using the cuff 12.

In the meantime, if a negative judgment is made at SC4, the control of the CPU goes to SC6 corresponding to the first-change-value-calculating means 80. At SC6, the CPU 56 determines, as a first change value, a first EBP difference $\Delta EBP1$ which is obtained by subtracting the systolic blood pressure $BP_{SYS}$ determined at SB6 of the control routing of FIG. 5, from the estimated blood pressure EBP determined at SC3, namely according to the following Expression (4):

$$\Delta EBP1 = EBP - BP_{SYS} \qquad \text{Expression (4)}$$

SC6 is followed by SC 7 to judge whether the first EBP difference $\Delta EBP1$ calculated at SC6 falls within the first reference range TH1 determined at SB9 of the control routine of FIG. 5. Described more specifically, at SC7, the CPU 56 judges whether the first EBP difference $\Delta EBP1$ is greater than the upper first threshold $TH1_U$ determined at SB9 or smaller than the lower first threshold $TH1_L$ determined at SB9. At this step, the CPU 56 judges whether or not a change of the current blood pressure from the blood pressure obtained by using the cuff 12 is abnormal. If an affirmative judgment is made at SC7, there is a high possibility that the blood pressure of the subject is abnormal. In this case, the CPU 56 caries out again the EBP-PWV relationship determining routine of FIG. 5 after execution of SC5 to indicate the blood pressure abnormality on the display device 62.

Subsequently, the control of the CPU 56 goes to SC8 corresponding to the second-change-value calculating means 82. At SC8, the CPU 56 determines, as a second change value, a second EBP difference $\Delta EBP2$ which is obtained by subtracting, from the estimated blood pressure EBP obtained at SC3, an estimated blood pressure which had been obtained at SC3 a predetermined time period before. The predetermined time period corresponds to the second-change-value-related time period determined at SA4 of the control routine of FIG. 4, i.e., four minutes in the present embodiment.

Subsequently, the CPU 56 carries out SC9 to judge whether an absolute value of the second EBP difference $\Delta EBP2$ determined at SC8 is greater than the second reference value TH2 (i.e., 40 mmHg in this embodiment) determined at SA7 of the control routine of FIG. 4. Namely, the CPU 56 judges whether a change of the blood pressure of the subject within a short period of time is large enough to indicate the abnormality of blood pressure. If an affirmative judgment is made at SC9, there is a high possibility that the blood pressure of the subject is abnormal. In this case, the CPU 56 carries out again the EBP-PVUV relationship determining routine of FIG. 5 after execution of SC5 to indicate the blood pressure abnormality on the display device 62. In the control routine of FIG. 6, SC4, SC5, SC7, and SC9 correspond to the abnormality judging means 98.

SC9 is followed by SC10 to judge whether a time period which has elapsed after the cuff-using BP measurement according to the control routine of FIG. 5 is longer than the calibration period $T_C$ pre-set at about 20 to 30 minutes. If a negative judgment is made at SC10, the CPU 56 repeats SC1 and the following steps. If an affirmative judgment is made at SC10, the CPU 56 carries out again the control routine of FIG. 5 to again determine another EBP-PWV relationship and another first reference range TH1.

In the embodiment employing the flow charts described above, a systolic blood pressure $BP_{SYS}$ actually obtained by using the cuff 12 is determined as a standard blood pressure $BP_{ST}$, and different first reference ranges TH1 are determined based on different standard blood pressures $BP_{ST}$. Accordingly, the first reference range TH1 can be appropriately determined, and the abnormality of blood pressure of the subject can be reliably judged.

Described more specifically, in the embodiment employing the above-described flow charts, the upper first threshold $TH1_U$ is determined such that the threshold $TH1_U$ decreases with the increase of the systolic blood pressure $BP_{SYS}$ actually obtained from the subject by using the cuff 12. Accordingly, the present arrangement determines the abnormality of blood pressure of the subject even if an increase of the blood pressure is relatively small where the systolic blood pressure $BP_{SYS}$ is relatively high. That is, the present arrangement prevents determination of the abnormality of blood pressure if an increase of the blood pressure is relatively large where the systolic blood pressure $BP_{SYS}$ is not so high. Further, the lower first threshold $TH1_L$ is determined such that the threshold $TH1_L$ increases, namely, the absolute value of the threshold $TH1_L$ decreases, with the decrease of the systolic blood pressure $BP_{SYS}$ actually obtained from the subject by using the cuff 12. Accordingly, the present arrangement determines the abnormality of blood pressure even if a decrease of the blood pressure is relatively small where the systolic blood pressure $BP_{SYS}$ is relatively low. That is, the present arrangement prevents determination of the abnormality of blood pressure if a decrease of the blood pressure is relatively large where the systolic blood pressure $BP_{SYS}$ is not so low. Thus, the present arrangement assures an accurate determination of the abnormal blood pressure.

In the BP monitor apparatus 10 constructed as described above, the relationship between first reference range and standard blood pressure can be inputted through the input device 54, so that the relationship is determined depending upon the circumstances. For instance, the relationship is determined for each specific operation in view of a medical judgment of the doctor in charge, the sort of the operation, and the physical power and age of each individual patient who undergoes the operation. If the first reference range TH1 is determined based on the relationship inputted through the input device 54, a first reference range TH1 can be appropriately determined, so that the abnormality of blood pressure can be determined with high accuracy.

In the BP monitor apparatus constructed as described above, if the relationship between first reference range and standard blood pressure is inputted through the input device 54, the relationship is recorded by the relationship recording means 90 on the recording medium 46 which is attachable to, and detachable from, the apparatus 10. Accordingly, the recording medium 46 on which the relationship has been recorded can be attached to another BP monitor apparatus, whereby the same blood pressure monitoring operation can be effected. Further, if the relationship is recorded on a plurality of recording media 46, the plurality of recording media 46 on which the common relationship is recorded are attached to a plurality of apparatuses, so that the same blood pressure monitoring operation can be effected in each of the plurality of apparatuses.

In the embodiment employing the above-described flow charts, the abnormality of blood pressure is determined when the absolute value of the second EBP difference ΔEBP2 is greater than the second reference value TH2 pre-set at 40 mmHg. The second EBP difference ΔEBP2 is indicative of an amount of change, during four minutes, of each estimated blood pressure value EBP determined for each pulse. Accordingly, the abnormality of blood pressure is determined based on not only the change of each of iteratively determined estimated blood pressure values EBP from the standard blood pressure $BP_{ST}$ (the systolic blood pressure $BP_{SYS}$), but also the change of each of the iteratively determined estimated blood pressure values EBP from the estimated blood pressure obtained the predetermined time period before the each estimated blood pressure. Therefore, the abnormality of blood pressure can be determined with high accuracy.

In the embodiment employing the above-described flow charts, the abnormality of blood pressure of the subject is determined when each of the estimated blood pressures EBP determined for respective pulses does not fall within the third reference range TH3 defined by the upper third threshold $TH3_U$ and the lower third threshold $TH3_L$, in other words, when each of the estimated blood pressures EBP is greater than the upper third threshold $TH3_U$ pre-set at 180 mmHg, or smaller than the lower third threshold $TH3_L$ pre-set at 80 mmHg. Therefore, the abnormality of blood pressure can be determined based on each estimated blood pressure value itself determined for each pulse, irrespective of the change of the each estimated blood pressure. Thus, an accurate determination of the abnormality of blood pressure is assured.

While the present invention has been described in detail in its presently preferred embodiment, by reference to the drawings, the invention may otherwise be embodied.

Figure 7:
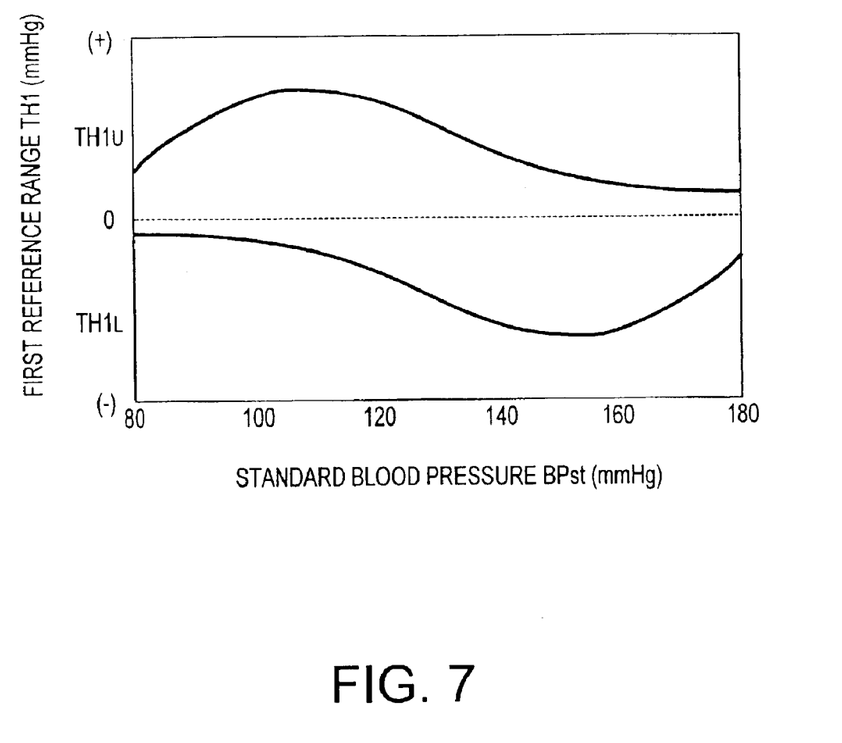
FIG. 7 is a view for explaining another relationship between first reference range and standard blood pressure.

For instance, in place of the relationship between first reference range and standard blood pressure, shown in the graph of FIG. 3, a different relationship between first reference range and standard blood pressure, shown in FIG. 7 may be employed. In the relationship of FIG. 7, upper and lower first thresholds $TH1_U$, $TH1_L$ smoothly change, as indicated by respective curved lines, with the decrease or increase of standard blood pressure $BP_{ST}$.

In the BP monitor apparatus 10 constructed as described above, the blood pressure BP obtained from the subject by using the cuff 12 is used as the standard blood pressure $BP_{ST}$ for determining the first change value. The estimated blood pressure EBP determined at any suitable time point may be used as the standard blood pressure $BP_{ST}$. Further, the standard blood pressure $BP_{ST}$ may be inputted through the input device 54.

The illustrated BP monitor apparatus 10 is adapted to iteratively obtain the pulse-wave propagation velocity PWV, determine the estimated blood pressure EBP based on the obtained pulse-wave propagation velocity PWV, and monitor the blood pressure of the subject based on the estimated blood pressure EBP. In place of the estimated blood pressure values EBP, blood pressure values iteratively obtained through a tonometric sensor may be employed. The tonometric sensor detects a pressure pulse wave produced from a suitable artery, such as a radial artery, on which the sensor is pressed via the skin, and blood pressure values are iteratively obtained based on the detected pressure pulse wave. Alternatively, the estimated blood pressure values EBP may be replaced with blood pressure values iteratively obtained in an invasive method using a catheter which is inserted into an artery of the subject.

In the BP monitor apparatus 10 constructed as described above, the second reference range TH2 and the third reference range TH3 are inputted through the input device 54. However, these ranges TH2, TH3 may be prescribed ranges that are pre-stored in the ROM 58.

In the BP monitor apparatus 10 constructed as described above, the relationship between first reference range and standard blood pressure is read from the recording medium 46 or inputted through the input device 54. However, the relationship may be pre-stored in the ROM 58.

The illustrated BP monitor apparatus 10 is adapted to monitor the blood pressure of the subject based on the systolic blood pressure $BP_{SYS}$. Alternatively, the BP monitor apparatus may be arranged to monitor the blood pressure of the subject based on the diastolic blood pressure $BP_{DIA}$ or the mean blood pressure $BP_{MEAN}$. Alternatively, at least two of the $BP_{SYS}$, $BP_{MEAN}$, and $BP_{DIA}$ may be employed to monitor the blood pressure.

The illustrated BP monitor apparatus 10 is adapted to measure the blood pressure BP from the subject by using the cuff 12, determine the pulse-wave propagation velocity PVW, and determine the estimated blood pressure EBP based on the pulse-wave propagation velocity PWV. However, the BP monitor apparatus need not be arranged to measure the blood pressure BP or determine the estimated blood pressure EBP, since the principle of the present invention is applicable to a central monitor device adapted to monitor the blood pressure of the subject based on blood pressure BP and estimated blood pressure EBP which are obtained by using respective separate devices.

It is to be understood that the present invention may be embodied with other changes, improvements and modifications that may occur to one skilled in the art without departing from the spirit and scope of the invention.

What is claimed is:

1. A blood pressure monitor apparatus for monitoring a blood pressure of a living subject, comprising:

a first-change-value calculating device for calculating a first change value as a change of each of a plurality of blood pressure values iteratively obtained from the subject, from a standard blood pressure obtained from the subject;

a relationship obtaining device for obtaining a relationship between first reference range and standard blood pressure wherein a plurality of different first reference ranges correspond to a plurality of different standard blood pressures, respectively;

a first-reference-range determining device for determining a first reference range based on the standard blood pressure obtained from the subject and according to the relationship between first reference range and standard blood pressure obtained by the relationship obtaining device; and an abnormality judging device for judging that the blood pressure of the subject is abnormal when the first change value calculated by the first-change-value calculating device does not fall in the first reference range determined by the first-reference-range determining device.

2. A blood pressure monitor apparatus according to claim 1, wherein the relationship between first reference range and standard blood pressure is determined by an operator of the blood pressure monitor apparatus.

3. A blood pressure monitor apparatus according to claim 2, wherein the relationship between first reference range and standard blood pressure is recorded on a recording medium which is attachable to, and detachable from, the apparatus.

4. A blood pressure monitor apparatus according to claim 1, wherein the first reference range is defined by an upper first threshold which is used to judge whether an increase of the blood pressure of the subject is abnormal, the relationship between first reference range and standard blood pressure being determined such that a smaller upper first threshold corresponds to a higher standard blood pressure.

5. A blood pressure monitor apparatus according to claim 1, wherein the first reference range is defined by a lower first threshold which is used to judge whether a decrease of the blood pressure of the subject is abnormal, the relationship between first reference range and standard blood pressure being determined such that a greater lower first threshold corresponds to a lower standard blood pressure.

6. A blood pressure monitor apparatus according to claim 1, further comprising:

a second-change-value calculating device for calculating a second change value as a change of said each of said blood pressure values from a blood pressure value obtained a predetermined time period before said each of said blood pressure values; and a second-reference range determining device for determining a second reference range;

wherein the abnormality judging device judges that the blood pressure of the subject is abnormal when the second change value calculated by the second-change-value calculating device does not fall in the second reference range is determined by the second-reference-range determining device.

7. A blood pressure monitor apparatus according to claim 6, further comprising:

a third-reference-range determining device for determining a third reference range;

wherein the abnormality judging device judges that the blood pressure of the subject is abnormal when said each of said blood pressure values does not fall in the third reference range determined by the third-reference-range determining device.

* * * * *